United States Patent [19]
Still et al.

[11] Patent Number: 5,740,072
[45] Date of Patent: Apr. 14, 1998

[54] RAPIDLY CONVERGENT METHOD FOR BOLTZMANN-WEIGHTED ENSEMBLE GENERATION IN FREE ENERGY SIMULATIONS

[75] Inventors: W. Clark Still, New York; Frank Guarnieri, Brooklyn; Hanoch Senderowitz, New York, all of N.Y.

[73] Assignee: The Trustees of Columbia Universuty in the City of New York, New York, N.Y.

[21] Appl. No.: 320,255

[22] Filed: Oct. 7, 1994

[51] Int. Cl.$^6$ .......................... G06F 17/50; G01N 37/00
[52] U.S. Cl. ...................... 364/499; 364/496; 364/578
[58] Field of Search ................................ 364/496, 499, 364/578

[56] References Cited

U.S. PATENT DOCUMENTS

| | | | |
|---|---|---|---|
| 5,293,455 | 3/1994 | Castelaz | 395/24 |
| 5,307,287 | 4/1994 | Cramer, III et al. | 364/496 |
| 5,331,573 | 7/1994 | Balaji et al. | 354/578 X |
| 5,424,863 | 6/1995 | Turner et al. | 354/578 |
| 5,434,796 | 7/1995 | Weininger | 364/496 |
| 5,448,498 | 9/1995 | Namiki et al. | 364/496 |

OTHER PUBLICATIONS

M.P. Allen, Molec Phys., 1980, 40, 1073–1087.

M.P. Allen and D.J. Tildesley, eds. Computer Simulation of Liquids, Clarendon Press, Oxford, 1987 pp. 1–18, 33–68, 71–109, 110–139, 140 212–231.

H.C. Andersen, J. Chem. Phys., 1980, 72, 2384–2393.

Burger, M.T., et al. (1994) Free Energy Calculations in Molecular Design: Predictions by Theory and Reality by Experiment with Enantioselective Podand Ionophores. J. Am. Chem. Soc. 116:3593–4.

Guarnieri, F. and Still, W.C. (1994) A Rapidly Convergent Simulation Method: Mixed Monte Carlo/Stochastic Dynamics, J. Computational Chemistry 15(11):1302–1310.

McDonald, D.Q. and Still, W.C. (1996) Application of Free Energy Perturbation Calculations to the Enantioselective Binding of Peptides to C3–Symmetric Synthetic Receptors. J. Am. Chem. Soc. 118:2073–2077.

P.K. Mehrotra, et al., J. Chem. Phys., 1983, 78, 3156–3266.

N. Metropolis and S. Ulam, J. Am. Stat. Assoc., 1949, 44, 335–341.

F. Mohamadi, et al., J. Comput. Chem., 1990, 11, 440–467.

C. Pangali, et al., Chem. Phys. Lett., 1978, 55, 413–417.

T.P. Straatsma and J.A McCammon, J. Chem. Phys., 1989, 90, 3300–3304.

T.P. Straatsma and J.A. McCammon, J. Chem. Phys., 1989, 91, 3631–3637.

W.C. Swope, et al., J. Chem. Phys., 1982, 76, 637–649.

W.F. van Gunsteren and H.J.C. Berendsen, Molec. Simul., 1983, 45,637–647.

W.F. van Gunsteren and H.J.C. Berendsen, Molec. Simul., 1988, 1, 173–185.

(List continued on next page.)

*Primary Examiner*—Edward R. Cosimano
*Attorney, Agent, or Firm*—John P. White

[57] ABSTRACT

The invention is directed to a method for generating possible conformations of a molecule comprising the steps of:

a) selecting a first conformation of the molecule characterized by a first set of coordinates associated with each atom in the molecule by the presence of a pattern of forces among such atoms and by a series of intrinsic forces associated with each atom;

b) varying the pattern of forces among such atoms in a non-random manner and randomly varying the series of intrinsic forces associated with each atom so as to generate a second conformation of the molecule characterized by a second set of coordinates associated with each atom in the molecule, by a second pattern of forces among each atom and by a second series of intrinsic forces associated with each atom; and c) randomly varying the second set of coordinates so as to obtain a third set of coordinates and thereby generating such possible conformations of the molecule.

2 Claims, 8 Drawing Sheets

OTHER PUBLICATIONS

X. Wang, et al., J. Am. Chem. Soc., 1992, 114, 4128–4137.

Heermann; "Computer Simulation Methods in Theoretical Physics"; Second Edition, Spinger–Verlag Berlin Heidelberg, pp. VII, IX, XI, & 1–145, 1990.

Metropolis et al; "Equation of State Calculations by Fast Computing Machines"; The Journal of Chemical Physics, vol. 21, No. 6, pp. title & 1087–1092, Jun., 1953.

Mitchell et al; "Free Energy Difference Calculations by Thermodynamic Integration: Difficulties in Obtaining a Precise Value"; Journal of Computational Chemistry, Volumen 12, No. 2, pp. Title & 272–275, Mar., 1991.

Press et al; "Numerical Recipes The Art of Scientific Computing"; Cambridge University Press, pp. Title, copyright, viii, & 454–459, 1986.

Ryckaert et al; "Numerical Integration of the Cartesian equations of Motion of a System with Constraints: Molecular Dynamics of n–Alkanes"; Journal of Computational Physics, 23, pp. cover & 327–341, 1977.

van Gunsteren et al; "On the Interpretation of Biochemical Data by Molecular Dynamics Computer Simulation"; European Journal of Biochemistry, vol. 204, No. 3, pp. cover, A5 & 947–961, Mar. 1992.

Wood; "Monte Carlo Studies of Simple Liquid Models"; Physics of Simple Liquids, Wiley Interscience Division, John Wiley & Sons, Inc. New York; pp. title, copyright, conents & 115–230, 1968.

Zwanzig; "High–Temperature Equation of State by a Perturbation Method"; The Journal of Chemical Physics, vol. 22, No. 8, pp. 1420–1426, Aug. 1954.

RAPIDLY CONVERGENT METHOD FOR BOLTZMANN-WEIGHTED ENSEMBLE GENERATION IN FREE ENERGY SIMULATIONS

BACKGROUND OF THE INVENTION

The invention disclosed herein was made with Government support under Grant No. CHE 92-08254 from the National Science Foundation. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains.

Impressive strides have recently been made in the development of free energy simulation methods; however, such simulations have yet to make a substantial impact as predictive tools for molecular design. The obvious impediments to such applications are the inaccuracies of contemporary molecular mechanics force fields and the difficulty in, obtaining converged, time-invariant results. Though considerable effort has been expended on improving force fields, it seems that the second issue, the ensemble sampling problem, is currently the limiting one in using free energy simulations as practical, predictive tools. The unfortunate result of inadequate ensemble sampling is that separate free energy simulations give different results depending upon initial conditions or on the length of time the simulation runs. Recent reports (M. J. Mitchell and J. A. McCammon, J. Comput. Chem., 1991, 12, 271; W. F. van Gunsteren and A. E. Mark, Eur. J. Biochem., 1992, 204, 947) suggest that many previously reported simulations (and by implication contemporary ones as well) were too short to give free energy results which are converged to sufficient precision (e.g. ±0.5 kcal/mol) for practical applications.

Adequate sampling is particularly difficult to attain when the system studied has multiple conformations separated by large energy barriers. The problem is that stable, converged free energies can be obtained only when all significantly populated conformational isomers are sampled with the correct statistical weights and when the local conformational space of each conformer is adequately sampled as well. Using standard simulation methods, sampling the different conformations of a system becomes highly inefficient when energy barriers separating conformers are large, because barrier-crossing then becomes a rare event. In the limit of a very large energy barrier, a classical simulation method would spend all of its time sampling the local space of the starting conformation only. In such a case, simulation results would appear converged but would not represent the ensemble average of the real molecule. Such problems are quite common with real molecular systems. Even the 3–5 kcal/mol torsional barriers which are characteristic of simple organic molecules can cause serious sampling problems in a simulation and lead to inadequate convergence (T. P. Straatsma and J. A. McCammon, J. Chem. Phys., 1989, 90, 3300; T. P. Straatsma and J. A. McCammon, J. Chem. Phys., 1989, 91, 3631). These problems can be largely overcome by the mixed Monte Carlo/Stochastic Dynamics method (MC/SD) and the Jumping Between Wells (JBW) smart monte carlo methods described herein. The Monte Carlo (MC) method is defined by representing the solution of a problem as a parameter of a hypothetical population, and using a random sequence of numbers to construct a sample of the population, from which statistical estimates of the parameter can be obtained (Heermann, Dieter W., Computer simulation methods in theoretical physics, 2nd ed., Berlin; New York: Springer-Verlag, c1990).

The MC method in simulational physics takes a different approach. It starts out with a description of the system in terms of a Hamiltonian, and an appropriate ensemble for the problem is selected. Then all observables are computable using the associated distribution function and the partition function. The idea is to sample the main contributions to get an estimate for the observable. The MC technique in statistical physics is centered around the computation of mathematical expectations (Heermann, Dieter W., Computer simulation methods in theoretical physics, 2nd ed., Berlin; New York: Springer-Verlag, c1990).

Before beginning a discussion of pure stochastic procedures examine hybrid methods. Such algorithms involve a deterministic part consisting of the integration of equations of motion. The components added to the deterministic part are stochastic forces influencing the path of the system through phase space. (Heermann, Dieter W., Computer simulation methods in theoretical physics, 2nd ed., Berlin; New York: Springer-Verlag, c1990).

In the Molecular-Dynamics (MD) method, all degrees of freedom are explicitly taken into account, leading to classical equations of motion of a system of particles. A trajectory of the system through phase space is constructed by numerically integrating the equations of motion, starting with some initial conditions. Observables are then calculated along the trajectory. In stochastic dynamics computer-simulation methods, of which Brownian dynamics is a special case, some degrees of freedom are represented only through their stochastic influence on the others. Suppose a system of particles interacts with a viscous medium. Instead of specifying a detailed interaction of a particle with the particles of the viscous medium, we represent the medium as a stochastic force acting on the particle. The stochastic force reduces the dimensionality of the dynamics.

The Brownian-Dynamics (BD) simulation algorithms described in the following all concern the problem of generating paths in phase space yielding a constant temperature. The detailed interaction of the particles with the heat bath is neglected, and only taken into account by the stochastic force (Heermann, Dieter W., Computer simulation methods in theoretical physics, 2nd ed., Berlin; New York: Springer-Verlag, c1990).

SUMMARY OF THE INVENTION

The invention is directed to a method for generating possible conformations of a molecule comprising the steps of:

a) selecting a first conformation of the molecule characterized by a first set of coordinates associated with each atom in the molecule by the presence of a pattern of forces among such atoms and by a series of intrinsic forces associated with each atom;

b) varying the pattern of forces among such atoms in a non-random manner and randomly varying the series of intrinsic forces associated with each atom so as to generate a second conformation of the molecule characterized by a second set of coordinates associated with each atom in the molecule, by a second pattern of forces among each atom and by a second series of intrinsic forces associated with each atom; and c) randomly varying the second set of coordinates so as to obtain a third set of coordinates and thereby generating such possible conformations of the molecule.

DETAILED DESCRIPTION OF THE INVENTION

The invention is directed to a method for generating possible conformations of a molecule comprising the steps of:

a) selecting a first conformation of the molecule characterized by a first set of coordinates associated with each atom in the molecule by the presence of a pattern of forces among such atoms and by a series of intrinsic forces associated with each atom;

b) varying the pattern of forces among such atoms in a non-random manner and randomly varying the series of intrinsic forces associated with each atom so as to generate a second conformation of the molecule characterized by a second set of coordinates associated with each atom in the molecule, by a second pattern of forces among each atom and by a second series of intrinsic forces associated with each atom; and c) randomly varying the second set of coordinates so as to obtain a third set of coordinates and thereby generating such possible conformations of the molecule.

A molecule as used herein refers to a molecule or a molecular system. A molecular system is defined as one or more molecules.

An intrinsic force as used herein may be a force acting on the atom which is a result of the forces of the environment the molecule is in. For example the atoms of a molecule in a solvent will have forces resultant from the collision of the solvent molecules with the atoms.

The method described above may also be performed step (c) first followed by step (b) to generate possible conformations of the molecule.

The method described above can also be used for generating a series of possible conformations of a molecule which comprises generating a possible conformation and then repeating such method to obtain one or more additional possible conformations, the selected first conformation of step (a) of each such repeated method being a possible conformation previously generated.

In addition the method described above can further be used for generating a collection of possible conformations of a molecule which comprises generating a possible conformation and then repeating such method to obtain one or more additional possible conformations, the selected first conformation of step (a) of each such repeated method being a possible conformation previously generated.

The methods described above utilize a molecule or molecular system having internal coordinates having an unconstrained global translation and rotation coordinates. Step (b) of the method may be performed using Langevin or Stochastic dynamics utilize a Velocity Verlet numerical integration method. Step (c) may be performed with Monte Carlo utilize a Metropolis Monte Carlo method (N. Metropolis, A. W. Rosenbluth, M. N. Rosenbluth, A. H. Teller, E. Teller, J. Chem. Phys. 21, 1087 (1953); Computer Simulation of Liquids, M. P. Allen and D. J. Tildesley, Clarendon Press, Oxford, 1987) or a Jumping Between Wells method.

In the methods described herein the conformation of the molecule or molecular system with internal coordinates may be stored in machine readable form before or after step (b). The conformation of the molecule or molecular system with internal coordinates may be sampled before or after step (b). Alternatively, the conformation of the molecule or molecular system with internal coordinates is sampled before or after step (c). The conformation of the molecule or molecular system with internal coordinates may be stored in machine readable form before or after step (c).

A property of the molecule or molecular system may be computed from the conformation with internal coordinates before or after step (b) of the method described herein. Alternatively, the property of the molecule or molecular system may be computed from the conformation with internal coordinates before or after step (c). The methods described above herein may be carried out in vacuo or in a condensed phase.

The invention also provides for a simulation method to generate a Boltzmann-weighted sample of significantly populated states of a molecule or molecular system having internal coordinates at a given temperature from which average properties of the molecule or molecular system may be calculated, comprising the steps of:

a) finding a set of distinct conformations of the molecule or molecular system;

b) constructing a set of internal coordinate variations that will interconvert pairs of conformations found in step (a);

c) choosing an arbitrary set of initial coordinates of the molecule or molecular system (X);

d) finding the conformation of the molecule or molecular system (Y) from step (a) that is most similar to (X);

e) choosing a conformation (Z) from step (a);

f) applying the internal coordinate variation from step (b) that converts conformation (Y) into conformation (Z) to convert the coordinates of the molecule or molecular system (X) to (Q);

g) using a Monte Carlo method to randomly vary one or more of the coordinates of the conformation (Q); and h) repeating steps (d) through (g) as many times as necessary to generate an electronic signal which corresponds to a stable ensemble of states from which average properties of the molecule or molecular system can be calculated.

In the method described above the Monte Carlo is a Metropolis Monte Carlo or a Jumping Between Wells method. The Metropolis Monte Carlo energy test compares the energies of coordinates of step (c) and the result of step (f). The conformation of the molecule or molecular system with internal coordinates may be stored in machine readable form before or after step (g). The conformation of the molecule or molecular system with internal coordinates may be sampled before or after step (g). The property of the molecule or molecular system for the method described above is computed from the conformation with internal coordinates before or after step (g).

Figure 1:
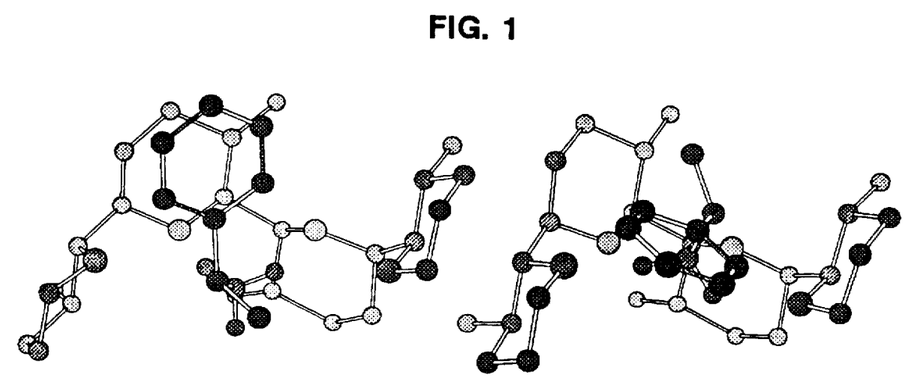
FIG. 1. Two forms of a conformationally homogeneous podand host and an alpha-phenethylammonium ion guest.

To illustrate the magnitude of the problem associated with even simple multiple minimum systems, take for example the bimolecular complex of a simple, conformationally homogeneous podand host and an alpha-phenethylammonium ion guest. This system has two low energy forms (FIG. 1) which are comparable in energy according to molecular mechanics (X. Wang, S. D. Erickson, T. Iimori and W. C. Still, J. Am. Chem. Soc., 1992, 114, 4128).

However, neither molecular nor stochastic dynamics at 300 K interconvert these forms during simulations lasting many hundreds of picoseconds (ps). Consequently, standard dynamics methodology would appear to require simulation times on the order of nanoseconds (ns) or longer to yield meaningful simulation results with such structures. More flexible or higher barrier systems could be orders of magnitude worse.

Because applicants wish to use free energy simulation as a tool for designing new molecular receptors which may have multiple binding conformations, applicants have devised a new simulation method which generates the canonical (Gibbs) ensemble efficiently with simple but conformationally flexible systems. The method combines the strengths of two common simulation methods: stochastic dynamics (SD) (W. F. van Gunsteren and H. J. C. Berendsen, Molec. Simul., 1988, 1, 173) which searches local space efficiently and Metropolis Monte Carlo (MC) (N. Metropolis and S. Ulam, J. Am. Stat. Assoc., 1949, 44, 335; W. W. Wood in Physics of Simple Liquids, H. N. V. Temperley, J. S. Rowlinson and G. S. Rushbrooke, Eds., North-Holland, Amsterdam, 1968, Chapter 5) which has the capacity to interconvert conformations separated by large energy barriers. Unlike previous approaches which mix MC-like procedures and dynamics, (W. F. van Gunsteren and H. J. C. Berendsen, Molec. Simul., 1988, 1, 173; C. Pangall, M. Rao and B. J. Berne, Chem. Phys. Lett., 1978, 55, 413; H. C. Andersen, J. Chem. Phys., , 1980, 72, 2384; P. K. Mehrotra, M. Mezei and D. L. Beveridge, J. Chem. Phys., 1983, 78, 3156) the method puts the two simulation procedures on an equal footing and involves alternating between SD and MC steps during the simulation. The result is a rapidly convergent method which is able to solve the sampling problem with many organic molecules and complexes including the podand system mentioned above.

The ability of the MC-SD method to generate canonical ensembles was tested with particles in simple double-well potentials and with the molecular system, n-pentane. The mixing method does not create artifacts and the final ensemble averages generated by MC, SD and MC-SD appear indistinguishable. It will also be shown that dynamics, the most commonly used method for free energy simulations with complex systems, can be extraordinarily inefficient relative to MC and MC-SD at generating converged ensembles even with molecular systems as simple as n-pentane.

Stochastic Velocity Verlet

The stochastic equation of motion with delta function memory is:

$$m\, dv/dt = f[x(t)] + R(t) - m\gamma v \qquad \text{I}$$

$$\langle R(t) R(t') \rangle = 2m\gamma kT\delta(t-t') \qquad \text{II}$$

Where m is the mass, v is the velocity, f is the deterministic force, γ is the friction coefficient, R is the random force, k is Boltzmann's constant, T is the temperature, and the pointed brackets indicate equilibrium ensemble averaging.

Dividing the equation of motion by m, adding γv to both sides, and multiplying by the integrating factor exp(γt), we obtain:

$$d/dt[\exp(\gamma t)v] = \exp(\gamma t)\{f[x(t)] + R(t)\}/m$$

Integrating from t to t+Δt:

$$v(t + \Delta t) = v(t)\exp(-\gamma\Delta t) + f(t)[1 - \exp(-\gamma\Delta t)]/(m\gamma) +$$

$$\exp(-\gamma t)/m \int_{t}^{t+\Delta t} dt' R(t')\exp(\gamma t')$$

$$x(t + \Delta t) = x(t) + v(t)[1 - \exp(-\gamma\Delta t)]/\gamma + \qquad \text{III}$$

$$f(t)\{\gamma\Delta t - [1 - \exp(-\gamma\Delta t)]\}/(m\gamma^2) +$$

$$1/(m\gamma) \int_{t}^{t+\Delta t} dt' R(t')\{1 - \exp[-\gamma(t + \Delta t - t')]\}$$

Let $R1(t, t + \Delta t) = 1/(m\gamma) \int_{t}^{t+\Delta t} dt' R(t')\{1 - \exp[-\gamma(t + \Delta t - t')]\}$ Integrating the position from t to t−Δt:

$$x(t - \Delta t) = x(t) + v(t)[1 - \exp(\gamma\Delta t)]/\gamma + \qquad \text{IV}$$

$$f(t)\{-\gamma\Delta t - [1 - \exp(\gamma\Delta t)]\}/(m\gamma^2) +$$

$$R1(t, t - \Delta t)$$

Solving equations III and IV simultaneously to eliminate v(t):

$$x(t + \Delta t) = x(t)[1 + \exp(-\gamma\Delta t)] -$$

$$x(t - \Delta t)\exp(-\gamma\Delta t) + f(t)\Delta t[1 - \exp(-\gamma\Delta t)]/(m\gamma) +$$

$$R1(t, t + \Delta t) + \exp(-\gamma\Delta t)R1(t, t - \Delta t)$$

Integrating the positions to x(t+2Δt), adding this to x(t+Δt), and recalling that velocity in the velocity Verlet MD algorithm is v(t)=[x(t+Δt)−x(t−Δt)]/(2Δt), the velocity integration in the velocity Verlet SD algorithm is:

$$v(t + \Delta t) = v(t)\exp(\gamma\Delta t) + \qquad \text{V}$$

$$[f(t) + f(t + \Delta t)][1 - \exp(-\gamma\Delta t)]/(2m\gamma) +$$

$$[R1(t, t + \Delta t) + R1(t + \Delta t, t + 2\Delta t)]/(2\Delta t) +$$

$$\exp(-\gamma\Delta t)[R1(t, t - \Delta t) + R1(t + \Delta t, t)]/(2\Delta t)$$

Equation III is the position integration and equation V is the velocity integration. The integrals of the random variables are solved by assuming that they obey Gaussian distributions with the time correlations given by equation II.

Method and tests with a double-well potential. The method that has been developed is based on the assumptions that:

1. dynamical methods (e.g. SD) do a good job of sampling phase space to generate a canonical ensemble for systems whose significantly populated states are not separated by large energy barriers;
2. MC methods can sample different conformational states to generate a canonical ensemble even when the barriers between states are large providing that sufficiently large trial steps are used; and 3. a mixing method can be devised which interleaves SD and MC steps in a unified simulation method which samples local and remote regions of phase space efficiently and generates a canonical ensemble.

A mixed MC-SD method which uses MC to drive the system from one conformation to another with the proper statistical weights and SD to sample the local space of each conformation has been developed. While alternating between MC and SD steps in a single simulation is simple enough, it was not obvious that a proper ensemble would result from such a procedure. It was also unclear how atomic velocities should be handled after a successful MC step. To evaluate the result of such alternations and of various alternative velocities treatments, double well potentials of the following form have been studied:

$$E = a_0 - a_1 x + a_2 x^2 - 2_3 x^3 + a_4 x^4$$

Potential 1: $a_0=33.070$, $a_1=28.835$, $a_2=10.506$, $a_3=1.568$, $a_4=0.082$

Potential 2: $a_0=33.339$, $a_1=30.082$, $a_2=11.382$, $a_3=1.738$, $a_4=0.092$

Potential 3: $a_0=33.713$, $a_1=31.711$, $a_2=12.693$, $a_3=1.997$, $a_4=0.107$

Potential 4: $a_0=36.537$, $a_1=40.802$, $a_2=18.166$, $a_3=2.975$, $a_4=0.160$

Figure 2:
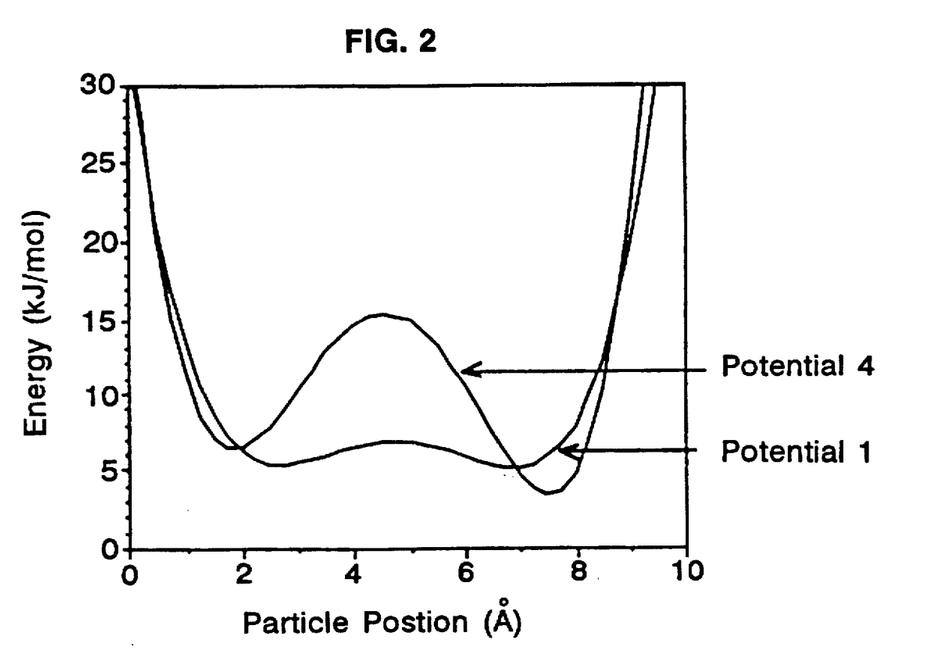
FIG. 2. Graph of potentials 1 and 4.

The coefficients ($a_0$–$a_4$) were chosen to give two unsymmetrical minima separated by barriers ranging from 1.7 kJ/mol (potential 1) to 12.0 kJ/mol (potential 4) (see FIG. 2). Because the barrier of potential 1 is low, it provides a system whose phase space can be explored efficiently by SD at 300 K. Potential 4, on the other hand, has a relatively large barrier which should be crossed only infrequently by SD at 300 K. Potentials 2 and 3 have barriers of intermediate height (2.9 and 5.2 kJ/mol).

A simple simulation program was written having both SD and MC modes for a one-dimensional oscillator having potential energy given by the expressions above. For the stochastic dynamics (SD) method, the leap-frog method described by van Gunsteren and Berendsen was used (W. F. van Gunsteren and H. J. C. Berendsen, Molec. Simul., 1988, 1, 173). For MC, the standard Metropolis method with a Boltzmann probability density function was used (N. Metropolis and S. Ulam, J. Am. Stat. Assoc., 1949, 44, 335; W. W. Wood in Physics of Simple Liquids, H. N. V. Temperley, J. S. Rowlinson and G. S. Rushbrooke, Eds., North-Holland, Amsterdam, 1968, Chapter 5). First, pure SD and MC simulations was shown to give the same ensemble averages with potential 1, the low-barrier potential which appears efficiently sampled by both SD and MC.

As measures of the properties of the ensemble averages, the first two moments of the potential energy distribution were taken (the average and standard deviation) and the particle populations in the two different wells. For the SD simulations, a mass of 100 amu was assigned to the particle and the simulation parameters were set as follows: 2 fs timestep, 1.5 ps$^{-1}$ frictional coefficient, 300 K temperature, 1 ns equilibration time, 20 ns total simulation time. Potential energy and particle position in the double-well system were recorded every 50 fs. For the MC simulations, a maximum step size of ±6 Å was used, a distance large enough to span both energy wells and essentially eliminate the effect of barrier height upon convergence rate. The length of the MC simulations was 2.5×10$^7$ steps and the temperature was 300 K. Potential energy and particle position were recorded every 20 MC steps.

For the mixed MC-SD simulations, beginning with 1 ns of equilibration using pure SD as described above followed by a 20 ns MC-SD simulation in which every SD timestep was followed by an MC step. Starting simply by having the velocities used in the dynamics be unaffected by the MC part of the simulation. Thus, whether an MC step was successful or not, the same velocities for the following SD step were used and these were given by the standard SD method (W. F. van Gunsteren and H. J. C. Berendsen, Molec. Simul., 1988, 1, 173). For both MC-SD and pure MC, the acceptance rate for the Monte Carlo steps was found to be ~35%. The results shown in Table 1 suggest that all three methods give essentially the same ensemble of states in the limit of a long simulation.

TABLE 1

Ensemble averages of MC, SD and MC-SD methods for a one-dimensional oscillator using double-well potentials.[a]

| | Simulation Method | PE Average[b] | PE Std Deviation[c] | Well 2 Population[d] |
|---|---|---|---|---|
| Potential 1 (barrier = 1.7 kJ/mol) | Stochastic Dynamics | 6.084 | 1.061 | 0.5151 |
| | Monte Carlo | 6.086 | 1.074 | 0.5136 |
| | Mixed MC-SD | 6.086 | 1.070 | 0.5138 |
| Potential 2 (barrier = 2.9 kJ/mol) | Stochastic Dynamics | 6.264 | 1.251 | 0.5753 |
| | Monte Carlo | 6.253 | 1.243 | 0.5790 |
| | Mixed MC-SD | 6.252 | 1.243 | 0.5795 |
| Potential 3 (barrier = 5.2 kJ/mol) | Stochastic Dynamics | 6.589 | 1.767 | 0.6676 |
| | Monte Carlo | 6.545 | 1.741 | 0.6743 |
| | Mixed MC-SD | 6.542 | 1.737 | 0.6743 |
| Potential 4 (barrier = 12.0 kJ/mol) | Stochastic Dynamics | 5.755 | 2.463 | 0.6703 |
| | Monte Carlo | 5.474 | 2.368 | 0.7547 |
| | Mixed MC-SD | 5.476 | 2.367 | 0.7544 |

[a]The quartic potential functions are described in the text and simulations were carried out at 300° K.;
[b]average potential energy (kJ/mol);
[c]potential energy standard deviation (kJ/mol);
[d]proportion of all sampled structures in the low energy well (right-most in FIG. 2).

In the simulations with potential 1, the lowest barrier potential which is easiest to sample, all three methods give similar results for both potential energy moments and energy well populations. However, as the barrier is increased (potentials 2–4), SD diverges more and more from the MC results because interconversion between the two wells becomes less and less frequent with SD. Thus the results of the 20 ns SD runs appear converged to three significant figures only in the case of potential 1 having the low 1.7 kJ/mol barrier. With MC, results appear fully converged regardless of the barrier height because the large 6 Å trial step spans the significantly populated region of the entire double well potential. As Table 1 shows, the results of the MC-SD runs are essentially the same as those from pure MC regardless of barrier height.

As a second test of the MC-SD method, the free energy difference between a particle in potential 1 and a particle in potential 2 was computed using numerical integration and free energy perturbation with SD and MC-SD. Using standard formulas defining the Helmholtz free energy difference between two states ($\Delta A$) and partition function (Z) (D. Chandler, "Introduction to Modern Statistical Mechanics," Oxford University Press, 1987, Chapter 6, pages 159–183), $$\Delta A = A_2 - A_1 = -RT \ln(Z_2/Z_1)$$

where $Z_n = \int \exp(-PE_n/RT)\, dr$ numerical integration of potentials 1 and 2 was used to establish $Z_2$ and $Z_1$. The free energy perturbation calculations used the standard expression from Zwanzig (R. W. Zwanzig, J. Chem. Phys., 1954, 22, 1420):

$$A_2 - A_1 = -RT\, ln<[\exp(PE_2 - PE_1)RT]>_1$$

where $<>_1$ indicates an ensemble average generated using potential 1. The results using SD and MC-SD to generate the ensembles are given in Table 2. In these simulations, one hundred different simulations (blocks) of the time period indicated were carried out and the individual block free energies were used to compute the standard deviations of $\Delta A$. Cpu times measured on a Hewlett Packard Model 720 workstation show that MC-SD is approximately 50% slower per timestep than pure SD.

TABLE 2

| | Free Energy Difference (kJ/mol) between Potentials 1 and 2. | | |
|---|---|---|---|
| Simulation Method | $\Delta A$ (Std Deviation) | ps/block | cpu time (sec) |
| SD | −0.2417 (0.421) | 0.05 | 5.2 |
| | −0.2814 (0.377) | 0.10 | 7.0 |
| | −0.2944 (0.295) | 0.50 | 21.2 |
| | −0.2802 (0.232) | 1.00 | 38.9 |
| | −0.2632 (0.090) | 10.0 | 358 |
| | −0.2611 (0.063) | 20.0 | 715 |
| | −0.2564 (0.028) | 100.0 | 3570 |
| MC-SD | −0.2508 (0.094) | 0.05 | 7.4 |
| | −0.2573 (0.068) | 0.10 | 10.5 |
| | −0.2525 (0.031) | 0.50 | 35.6 |
| | −0.2541 (0.022) | 1.00 | 65.0 |
| | −0.2560 (0.007) | 10.0 | 614 |
| | −0.2566 (0.005) | 20.0 | 1220 |
| | −0.2566 (0.003) | 50.0 | 2382 |

As the data in Table 2 indicates, both SD and MC-SD converge to similar values for $\Delta A$ and both are very close to the −0.2567 kJ/mol found by direct numerical integration. The rates of convergence are, however, very different as are the standard deviations of the free energies obtained. The $\Delta A$ evaluated using the MC-SD simulation is converged to two significant figures with a simulation using one hundred 0.10 ps blocks and appears converged to three figures by the time 10.0 ps blocks are used. The analogous simulations using pure SD converge at least two orders of magnitude more slowly even though the ensemble was generated using the lowest barrier potential function. With the larger barrier potentials, the advantage of MC-SD over SD would be greater.

Thus the ensemble of structures generated by MC, SD and MC-SD methods appears to be the same with the simple double-well oscillator studied, and the MC and MC-SD methods substantially outperform pure SD in attaining convergence.

This invention will be better understood from the Experimental Details which follow. However, one skilled in the art will readily appreciate that the specific methods and results discussed are merely illustrative of the invention as described more fully in the claims which follow thereafter. Tests with n-pentane.

To test the MC-SD method on a more chemically relevant system n-pentane was chosen as a simple multiatomic structure having multiple, significantly populated conformations. As with the oscillator tests above, the tests involved comparing MC, SD and MC-SD simulation methods for their ability to generate the same (canonical) ensemble of states. To judge the ensembles generated, the first four moments of the potential energy distribution (average, standard deviation, skew and kurtosis as defined in W. H. Press, B. P. Flannery, S. A. Teukolsky and W. T. Vetterling, "Numerical Recipes," Cambridge University Press, 1986, pages 455–459) and the populations of pentane's nine conformational isomers were accumulated.

The pentane simulations were carried out on the united atom (5-particle) representation of n-pentane using the AMBER force field (S. J. Weiner, P. A. Kollman, D. A. Case, U. C. Singh, C. Ghio, G. Alagona, S. Profeta and P. Weiner, J. Am. Chem. Soc., 1984, 106, 765). The calculations were performed on Hewlett Packard Model 720 workstations using the MacroModel V4.5 (F. Mohamadi, N. G. J. Richards, W. C. Guida, R. Liskamp, M. Lipton, C. Caufield, G. Chang, T. Hendrickson and W. C. Still, J. Comput. Chem., 1990, 11, 440) distribution of BatchMin whose performance was verified by comparing MC, SD and MC-SD oscillator results with the above-described special purpose simulation program. The BatchMin SD used the stochastic leap-frog method (W. F. van Gunsteren and H. J. C. Berendsen, Molec. Simul., 1988, 1, 173). The MC employed the standard Metropolis method (N. Metropolis and S. Ulam, J. Am. Stat. Assoc., 1949, 44, 335; W. W. Wood in Physics of Simple Liquids, H.N.V. Temperley, J. S. Rowlinson and G. S. Rushbrooke, Eds., North-Holland, Amsterdam, 1968, Chapter 5) with energy increases greater than 100 kJ/mol always being rejected. The MC-SD simulation method was implemented as described above for the one-dimensional oscillator.

A variant of MC-SD which is compatible with SHAKE has not yet been developed, hence the simulations were carried out without constraints (J.-P. Ryckaert, G. Ciccotti and H. J. C. Berendsen, J. Comput. Phys., 1977, 23, 327. For MC-SD simulations in the absence of SHAKE with molecules having fast-moving particles such as hydrogens, a timestep of $\leq 1.0$ fs should be used).

In the first tests with polyatomic systems, it was found that the actual temperatures of converged MC-SD simulations were 20–30 K higher than the nominal 300 K temperature used in the MC and SD parts of the method. It was also found that the extent of heating varied with the MC acceptance rate. Based on the assumption that this excess kinetic energy might result from numerical inaccuracies in the SD integration method which anticipates smooth changes in velocities and forces from simulation step to step, the SD timestep was reduced and indeed a closer agreement was found between actual and nominal temperatures. With a timestep of 0.15 fs in a nominal 300 K MC-SD simulation, the actual temperature converged to 304 K. To limit the integration errors and still maintain a reasonable dynamics timestep, a modified MC-SD method was implemented and tested which used a 1.5 fs timestep for the SD portion of the method but which reduced the timestep to 0.15 fs for the twenty timesteps following any accepted MC move.

Upon analyzing the effect of random internal coordinate changes on various dynamics integration methods (W. F. van Gunsteren and H. J. C. Berendsen, Molec. Simul., 1988, 1, 173; W. F. van Gunsteren and H. J. C. Berendsen, Molec. Phys., 1983, 45, 637; M. P. Allen, Molec. Phys., 1980, 40, 1073) it was concluded that the velocity Verlet method (W. C. Swope, H. C. Andersen, P. H. Berens and K. R. Wilson, J. Chem. Phys., 1982, 76, 637) would be the most compatible with intervening MC moves because it is a forward-looking method which generates new positions and velocities exclusively from information available at the current timestep:

$x(t+Dt)=x(t)+v(t)Dt+f(t) \, Dt^2/(2m)$ $v(t+Dt)=v(t)+[f(t)+f(t+Dt)]Dt/(2m)$

In contrast, the leapfrog, Verlet and Beeman methods utilize information from previous timesteps which is undefined immediately following a successful MC move. Hence a stochastic equivalent of the velocity Verlet method was derived and implemented in the MC-SD simulation code. Tests with a simple harmonic oscillator and n-pentane (1.0 fs timestep) gave actual simulation temperatures within 0.5 degrees of the nominal simulation temperature (300 K) regardless of the MC acceptance rate. Results of the new SD and MC-SD methods with n-pentane are detailed in the following paragraphs.

Because n-pentane has nine distinct conformations which are separated by energy barriers of 12–25 kJ/mol, very long simulations were used in an attempt to achieve full convergence. In the case of SD and MC-SD, available resources allowed the use of total simulation times of 1 μs. Both SD and MC-SD simulations used a dynamics timestep of 1.5 fs, a frictional coefficient of 1.5 ps$^{-1}$, and an equilibration period of 10 ns. In the MC-SD simulations, only torsion angles were varied (±180°) by the Monte Carlo part of the method on the assumption that SD would adequately sample local degrees of freedom such as stretching and bending. The simulations themselves were carried out in ten blocks of 100 ns each. With pure MC, a series of simulations totaling 5×10$^8$ steps with variation of all degrees of freedom was used. The MC trial moves were limited to ±180° for torsion angles, ±3° for bond angles and ±0.05 Å for bond lengths. These large torsional variations were found to provide faster convergence than the smaller variations which are traditionally chosen to give acceptance rates of 30–40% (see below). The use of large torsional variations resulted in acceptance rates of 5.0% for MC and 6.7% for MC-SD. Potential energies and conformational population data were saved every ten steps with all simulation methods. Conformations of n-pentane were characterized by its two torsion angles in which each angle was designated as anti (a, 180°±30°), −gauche (−g, −60°±30°) or +gauche (+g, +60°±30°).

The energetic results of the three different simulations are summarized in Tables 3 and 4 below. These simulations were all carried out at nominal temperatures of 300 K. All three methods ultimately gave potential energy distributions whose moments are essentially identical. One of the most remarkable findings is that simple stochastic dynamics (SD) takes an extraordinarily longtime to give reasonably converged results, even with such a simple system as n-pentane. Thus after a full microsecond of SD, the average potential energy was just barely converged to the nearest 0.1 kJ/mol and the conformational populations were converged to only ±5%.

TABLE 3

Moments of energy distribution in various n-pentane simulations.

| Simulation Method | Simulation Length | Potential Energy (kJ/mol) | | | |
|---|---|---|---|---|---|
| | | Average | Std. Dev. | Skew | Kurtosis |
| MC | 1 × 10$^6$ | 12.31 | 5.67 | 0.83 | 1.04 |
| | 1 × 10$^7$ | 12.43 | 5.74 | 0.84 | 1.06 |
| | 5 × 10$^7$ | 12.44 | 5.71 | 0.84 | 1.08 |
| | 1 × 10$^8$ | 12.44 | 5.72 | 0.85 | 1.09 |
| | 5 × 10$^8$ | 12.45 | 5.73 | 0.85 | 1.10 |
| SD | 15 ns | 12.42 | 5.72 | 0.86 | 1.15 |
| | 45 ns | 12.42 | 5.72 | 0.86 | 1.12 |
| | 100 ns | 12.30 | 5.74 | 0.86 | 1.13 |
| | 300 ns | 12.33 | 5.71 | 0.85 | 1.12 |
| | 500 ns | 12.38 | 5.73 | 0.85 | 1.12 |
| | 1000 ns | 12.43 | 5.73 | 0.85 | 1.11 |
| MC-SD | 1 ns | 12.45 | 5.83 | 0.89 | 1.27 |
| | 2 ns | 12.43 | 5.78 | 0.87 | 1.17 |
| | 3 ns | 12.45 | 5.78 | 0.86 | 1.13 |
| | 4 ns | 12.46 | 5.78 | 0.87 | 1.16 |
| | 6 ns | 12.44 | 5.77 | 0.87 | 1.16 |
| | 14 ns | 12.45 | 5.75 | 0.86 | 1.13 |

TABLE 4

Populations of conformers in various n-pentane simulations.

| Simulation Method | Simulation Length | Conformational Population | | | | | | | | |
|---|---|---|---|---|---|---|---|---|---|---|
| | | a,a | a,+g | a,−g | +g,a | −g,a | +g,+g | −g,−g | +g,−g | −g,+g |
| MC | 1 × 10$^6$ | .405 | .121 | .120 | .119 | .113 | .037 | .036 | .0032 | .0032 |
| | 1 × 10$^7$ | .410 | .117 | .117 | .119 | .118 | .038 | .038 | .0031 | .0030 |
| | 5 × 10$^7$ | .408 | .118 | .119 | .118 | .118 | .038 | .038 | .0031 | .0031 |
| | 1 × 10$^8$ | .408 | .118 | .118 | .118 | .118 | .038 | .038 | .0031 | .0031 |
| | 5 × 10$^8$ | .408 | .118 | .118 | .118 | .118 | .038 | .038 | .0031 | .0031 |
| SD | 15 ns | .402 | .132 | .133 | .072 | .142 | .028 | .048 | .0008 | .0051 |
| | 45 ns | .457 | .123 | .103 | .089 | .131 | .024 | .030 | .0018 | .0043 |
| | 100 ns | .446 | .107 | .112 | .086 | .136 | .030 | .040 | .0021 | .0030 |
| | 300 ns | .429 | .110 | .102 | .123 | .128 | .036 | .031 | .0023 | .0024 |
| | 500 ns | .421 | .117 | .107 | .118 | .121 | .040 | .033 | .0026 | .0028 |
| | 1000 ns | .408 | .117 | .119 | .115 | .120 | .039 | .040 | .0030 | .0027 |
| MC-SD | 0.75 ns | .413 | .116 | .118 | .117 | .117 | .036 | .038 | .0026 | .0031 |
| | 1.5 ns | .414 | .115 | .116 | .118 | .117 | .037 | .038 | .0029 | .0030 |
| | 3.6 ns | .408 | .119 | .117 | .119 | .118 | .037 | .037 | .0028 | .0028 |
| | 6 ns | .408 | .118 | .118 | .119 | .118 | .038 | .038 | .0028 | .0029 |
| | 14 ns | .408 | .118 | .118 | .118 | .118 | .038 | .038 | .0029 | .0030 |

In comparison with the results of pure SD, conformer populations by MC and MC-SD approached convergence much more rapidly. The MC-SD simulation were particularly well converged, giving stable energy distributions and populations in less than 4 ns. Conformational population convergence can be estimated not only by the stability of the average populations of the various conformers but also by comparison of populations of molecular conformations which are equivalent by symmetry. Thus the populations of a,+g, a,−g, +g,a, −g,a conformers must all be the same in the limit as must be the populations of +g,+g, −g,−g and +g,−g, −g,+g conformers. As Table 4 shows, these equivalent conformer sets are equally populated to only two significant figures by velocity Verlet SD even after a lengthy 1 µs simulation. Leapfrog SD gave similar results. MC is significantly better in reaching convergence, but MC-SD is the most rapidly convergent method giving populations which are stable to almost three significant figures within 5 ns of simulation. Even after a short 1 ns MC-SD simulation, the conformational populations of n-pentane were all within 4% of their final values and had fluctuations closely resembling the thousand-fold longer 1 µs SD populations.

From the final populations found by the three simulations, the corresponding free energy differences between extended (a,a) and gauche (a,g) n-pentane conformations can be calculated to be 3.09 (MC), 3.05–3.15 (SD) and 3.09 (MC-SD) kJ/mol. In comparison, the standard normal mode analysis with the same force field gives a corresponding free energy difference of 3.14 kJ/mol.

Figure 3:
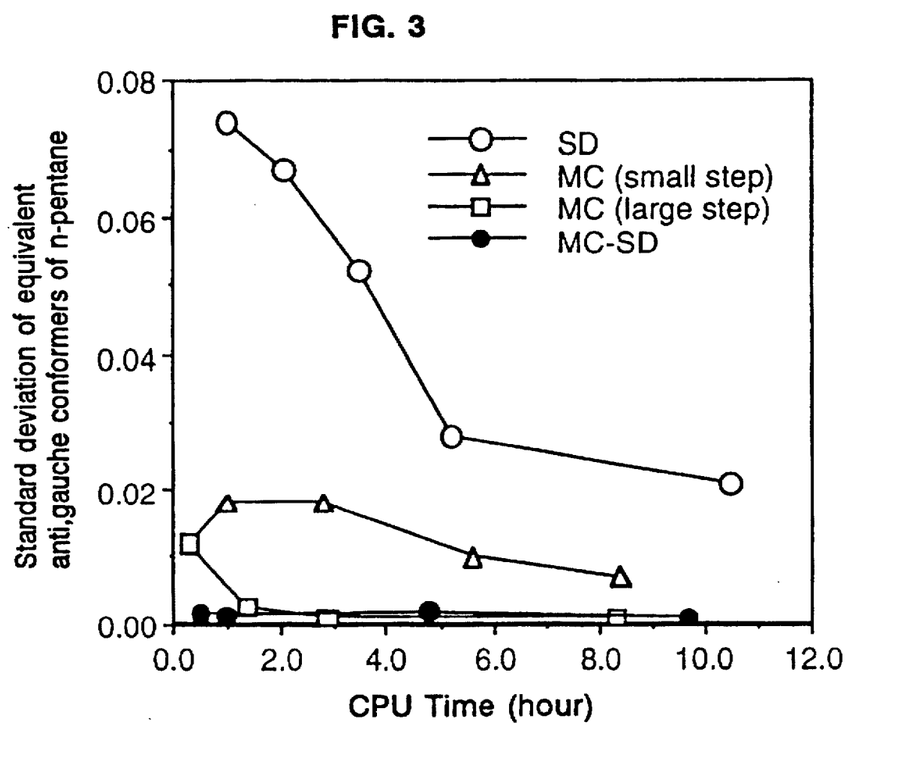
FIG. 3. Convergence Rates of Various Simulation Methods with n-Pentane.

To estimate the rate of convergence of the three methods based on computer (CPU) time, the standard deviations of populations of the four symmetry-equivalent anti,gauche conformations of n-pentane at various CPU times were tabulated. The results for each method are shown in FIG. 3. As indicated above, SD converges the slowest and MC-SD converges the fastest. The MC simulations were carried out in two different ways. First torsion angle variations were used that were small enough (maximum step =±30°) to give a traditional 30–40% acceptance rate. These data are shown in FIG. 3 as 'MC (small step)'. The 'MC (large step)' entry gives results for the ±180° torsional variations (5% acceptance rate) and shows significantly faster convergence.

Therefore by mixing classical stochastic dynamics (SD) and Monte Carlo (MC) simulation methods, a new hybrid MC-SD method has been developed which samples phase space in the systems studied more effectively than does SD or MC alone and generates a canonical ensemble.

MC-SD gave converged populations at a rate 2-3 orders of magnitude faster than pure SD in systems having ≧3 kcal/mol barriers between significantly populated states. The differences in rates of convergence between MC and MC-SD are smaller though the MC-SD method appears to converge more rapidly than MC by a factor of ~5 in the simple systems studied here. The advantage of MC-SD over MC is expected to grow significantly when cyclic systems are studied because of the tightly coupled internal coordinates of rings. For simulations in solution, the MC-SD method is compatible only with continuum treatments of solvent, because explicit solvent molecules limit the ability of the MC part of the method to make large, barrier-crossing movements. When used with a continuum solvation treatment, however, MC-SD can be used to generate high precision simulation results at a small fraction of the cost of dynamical methods.

The MC-SD method was also applied to more challenging molecular systems such as the podand ionophore complexes mentioned in the introduction. With these systems, MC-SD not only gave highly converged free energy simulation results but for the first time provided access to both retrospective and predictive calculations of binding enantioselectivity which were verified by experiment (M. T. Burger, A. Armstrong, F. Guarnieri, D. Q. McDonald and W. C. Still, J. Am. Chem. Soc., 1994, 116, 3593–3594).

Although superior to both parent methods, the mixed-mode technique still suffers from a major deficiency of Metropolis Monte Carlo (MMC). Since trial moves are chosen at random, most of them end up at high energy regions of the potential surface and are therefore rejected. This leads to a slow interconversion between conformers, manifested as small acceptance rate. Clearly, much could be gained by replacing MMC by a more efficient, rapidly converging, MC procedure. Several such modifications of MMC are found in the literature and are usually referred to as "Smart Monte Carlo," (N. Metropolis, A. W. Rosenbluth, M. N. Rosenbluth, A. Teller, E. Teller, J. Chem. Phys. 1953, 21, 1087; M. Rao, C. Pangali, B. J. Berne, Mol. Phys. 1979, 37, 1773; C. Pangali, M. Rao, B. J. Berne, Chem. Phys. Lett. 1978, 55, 413; M. Rao, B. J. Berne, J. Chem. Phys. 1979, 71, 129; J. Cao, B. J. Berne, J. Chem. Phys. 1990, 92, 1980; P. J. Rossky, J. D. Doll, H. L. Friedman, J. Chem. Phys. 1978, 69, 4628; S. Goldman, J. Chem. Phys. 1983, 79, 3938; M. Mezei, K. A. Bencsath, S. Goldman, S. Singh, Molecular Simulation 1987, 1, 87; M. J. Kotelyanskii, U. W. Suter, J. Chem. Phys. 1992, 96, 5383; T. Noguti, N. Go, Biopolymers 1985, 24, 527; C-Y. Shew, P. Mills, J. Phys. Chem. 1993, 97, 13824; R. Abagyan, M. Totrov, J. Mol. Biol. 1994, 235, 983; M. E. Clamp, P. G. Baker, C. J. Stirling, A. Brass, J. Comput. Chem. 1994, 15, 838; C-Y Schew, P. Mills, J. Phys. Chem. 1993, 93, 13824; R. Abagyan, M. Trotrov, J. Mol. Biol. 1994, 235, 983; M. E. Clamp, P. G. Baker, C. J. Stirling, A. Brass, J. Comput. Chem. 1994, 15, 838). None of them however seemed either directly applicable to molecular systems or highly efficient in interconverting between minimum energy conformers.

Figure 7:
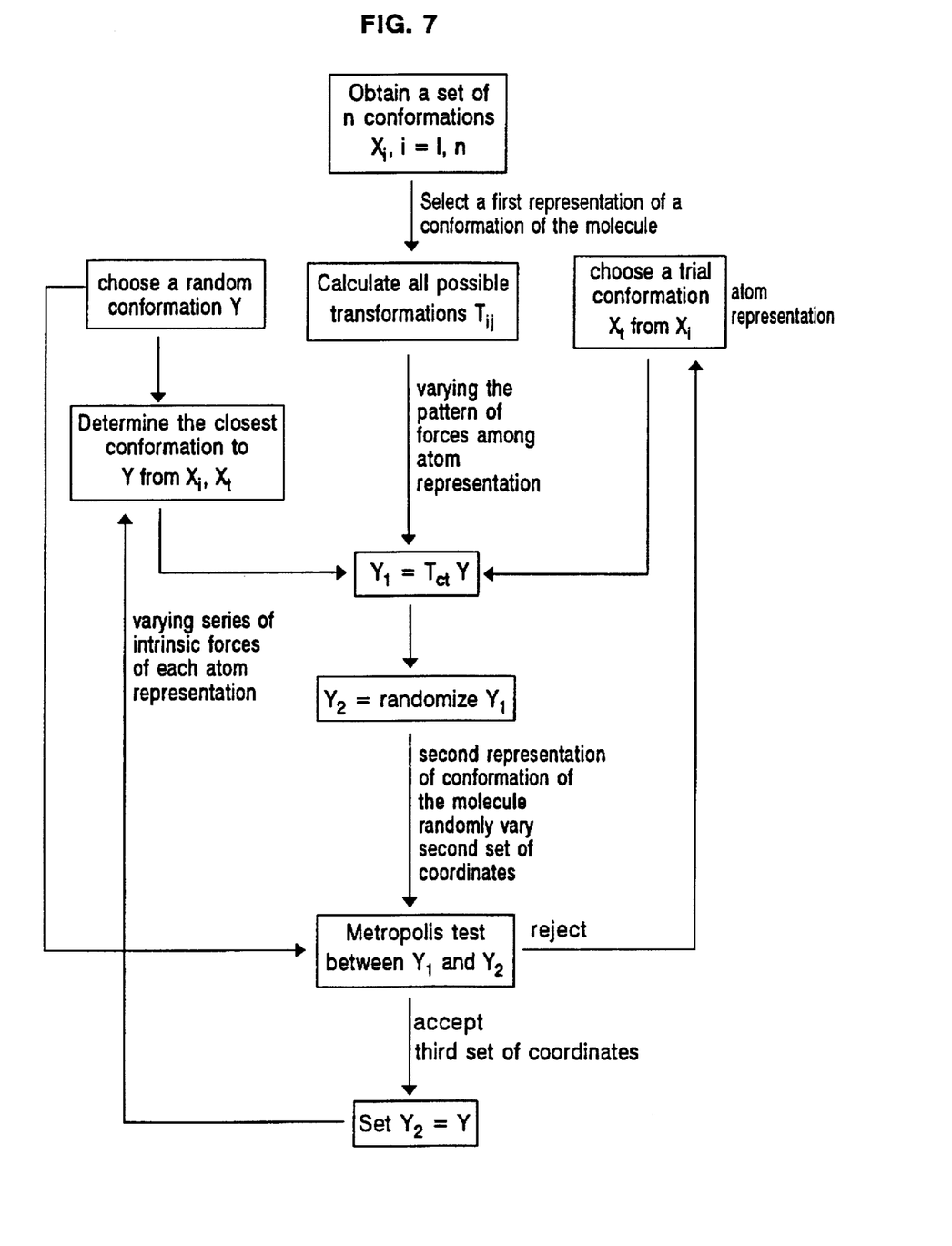
FIG. 7. A schematic representation of Jumping bewtween wells.

The modification of MMC is described as part of this invention. The method, which is termed "Jumping Between Wells" (JBW) See FIG. 7) takes advantage of previous knowledge on the location of minima or other important conformations on the potential surface in order to drive the simulation, preferably, to these regions. Although aimed to be used primarily as a replacement for MMC in the mixed mode procedure, JBW was developed as a stand alone MC method. Indeed, only when proven to produce the correct canonical ensemble, can it safely be integrated into the mixed-mode.

The smart Monte-Carlo method assumes that previous knowledge of the conformational surface can be used to drive the simulation towards its most significant regions. In particular, a series of molecular conformations (mainly minima but other important conformations may also be included), attainable from a conformational search or short SD runs, can serve this purpose. This latter can be used to assess the simulation convergence by sampling structures along the trajectory, minimizing them and verifying that the entire potential surface has indeed been sampled. Clearly, a simulation may produce a set of seemingly converged molecular properties when trapped, due to high energy barriers, in a subspace of the surface.

The essence of the method is the selection of a trial conformation with a probability heavily biased towards the low energy regions of the potential surface by making a move towards a randomly chosen minima. Once such an attempt is made, the usual Metropolis criterion is applied in order to accept/reject the move. Specifically, the following steps are involved:

1. Obtain a set of n conformations $X_i$, i=1, n and calculate all possible transformations between them $-T_{ij}$;

2. specify an initial conformation on the potential surface -Y0;
3. find a member of the Xi list which is closest to Y0-Xc;
4. randomly choose a trail conformation from the Xi list -Xt;
5. obtain a trail conformation -Y1 by applying Txcxt to Y0. Note that this procedure will create a minimum energy trail conformation only when Y0 is a member of the Xi list. In all other cases regions of the potential surface will be attempted. Creating a trial conformation which always coincides with a member of the Xi list by construction Tyoxt and applying it to Y0, can be shown to violate the principle of detailed balance of microscopic reversibility;
6. subject Y1 to an additional random conformational change, thereby obtaining conformation Y2. Failure to do so will result in the simulation being trapped in a subspace consisting of the members of the Xi list only;

arbitrary points on the potential surface and run for a total of $60\times10^6$ and $120\times10^6$ steps for the 1D and 2D surfaces, respectively. For MMC a maximum step size of 10Å was used along all relevant axes and for JBW, the transformation between two arbitrary wells, 1 and 2, consisted of the $X_2-X_1$ (and $Y_2-Y_1$) vectors with a randomization of 0.5 Å in each direction.

The data in Table 5 shows that both methods converge to the same limiting values which also coincide with those obtained by numeric integration, and therefore suggest that JBW generates the correct canonical ensemble. The acceptance rate of the method however, far exceeds that of MMC.

TABLE 5

A comparison of potential energy (PE; KJ/mol), standard deviation (SD), wells population and acceptance rates (% acceptance) between Numeric Integration (NI) using the Trapeze method, Metropolis Monte Carlo (MMC) and Jumping Between Wells (JBW) for potentials 1a-c.

|  | 1a | | | 1b | | | 1c | | |
| --- | --- | --- | --- | --- | --- | --- | --- | --- | --- |
|  | NI | MMC | JBW | NI | MMC | JBW | NI | MMC | JBW |
| PE | 1.247 | 1.244 | 1.247 | 2.494 | 2.511 | 2.494 | 3.700 | 3.701 | 3.701 |
| SD | 1.764 | 1.764 | 1.765 | 2.494 | 2.511 | 2.494 | 3.778 | 3.784 | 3.776 |
| Well 1 | 0.500 | 0.500 | 0.500 | 0.500 | 0.500 | 0.500 | 0.021 | 0.021 | 0.021 |
| Well 2 | 0.500 | 0.500 | 0.500 | 0.500 | 0.500 | 0.500 | 0.841 | 0.840 | 0.841 |
| Well 3 |  |  |  |  |  |  | 0.004 | 0.004 | 0.003 |
| Well 4 |  |  |  |  |  |  | 0.135 | 0.136 | 0.136 |
| Well 5 |  |  |  |  |  |  | .0001 | .0001 | .0001 |
| % acceptance |  | 0.053 | 0.595 |  | .0008 | 0.153 |  | .0007 | 0.047 |

7. use the metropolis test to compare Y0 and Y2, i.e., accept Y2 with a probability:

$$p=\min\{1,\exp[-\beta(Ey2-Ey0)]\}$$

where $\beta=1/kT$; and
8. go back to step 2.

The procedure outlined in stages 1-8 above results in the generation of a markov chain with the metropolis transition probabilities and consequently, a canonical ensemble. Since it employs previous knowledge on the potential surface, it was expected to substantially accelerate convergence in cases where there are only few minima and in particular, when these are deep and narrow, a situation often rising when multiple hydrogen bonds or strong electrostatic interactions are involved. In all other cases, the procedure should perform at least as good as MMC, provided all important conformations have been supplied as an input.

Tests with 1-dimensional and 2-dimensional surfaces

Figure 4A:
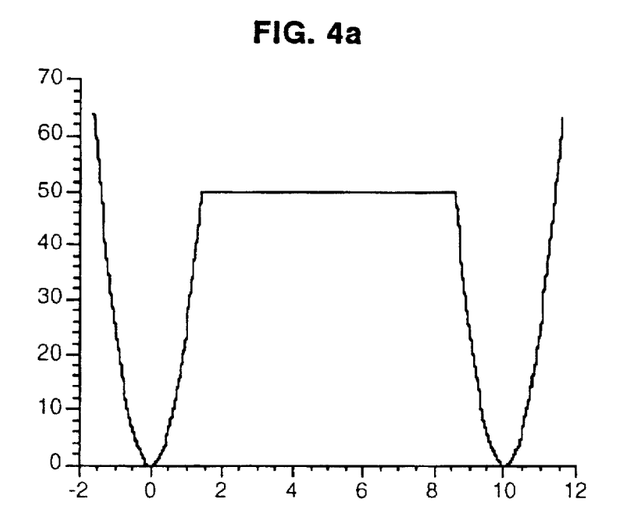
FIGS. 4a, 4b and 4c. Graphic representations of potentials 4a–c (energy in kJ/mol vs. particle position in Å).
Figure 4B:
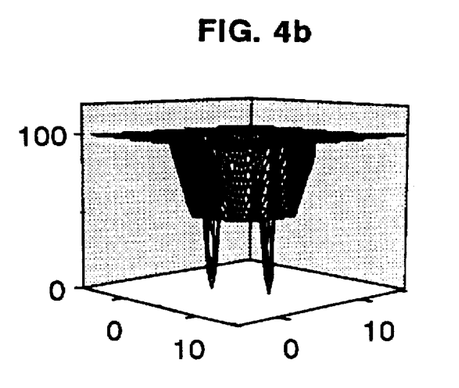
Figure 4C:
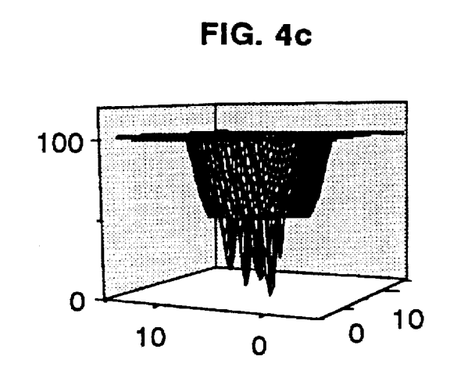

At the start the new method was incorporated into a program and tested on several 1D and 2D potential surfaces (FIGS. 4a, 4b and 4c). These were designed to reflect situations in which the method was believed to have a distinct advantage over MMC, and are therefore characterized by a small number of narrow, deep minima, separated by large, high energy barriers. As measures of the properties of the ensemble averages, the first two moments of the potential energy (average and standard deviation) and the populations of the different wells were taken. Due to the simplicity of the surfaces, the "correct" results from numeric integration could be obtained using the Trapeze method. Both the MMC and JBW simulations were initiated from Next, the relative efficiency of the two methods was considered. This, in principle, can be done by monitoring the convergence of either the moments of the potential energy or the wells population along the trajectory. However, for the symmetric surfaces (4a and 4b), only the second parameter can serve this purpose since perfectly correct energetic results can be obtained by sampling only half of the potential surface.

Figure 5A:
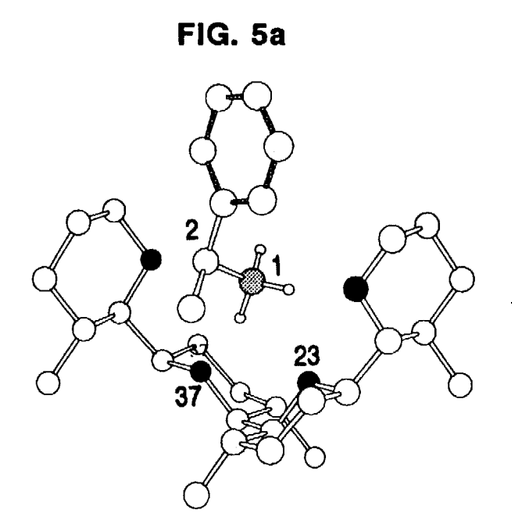
FIGS. 5a and 5b. Two binding modes of the podand ionophore complex as obtained from a rigid body conformational search. Numbered atoms define the torsional angle monitored during the simulations (see text). 5a: global minimum, E=−92.1 KJ/mol; 2b: minimum, E=−88.5 KJ/mol.

Potential as shown in FIG. 5a is the simplest case. It consists of two identical parabolic wells separated by a constant energy plateau. Since the latter is set to 50 KJ, its population is negligible and the limiting populations of the two minima are therefore 0.5 each. The total length of the potential below the E=100 KJ level is 14 Å, out of which, 5.6 Å (40%) are contained within the wells. Therefore JBW was expected to perform only moderately better than MMC, as indeed indicated by the results shown in Table 6. Both methods are converged to 2 decimal places after $3\times10^5$ steps but while JBW is almost converged from the start (maximum difference between the two populations is 0.02), the fluctuations in MMC are more pronounced (maximum difference between the two populations is 0.06).

Figure 5B:
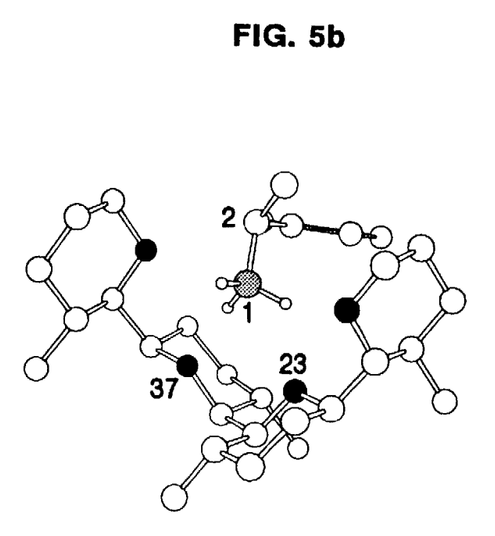
Figure 6A:
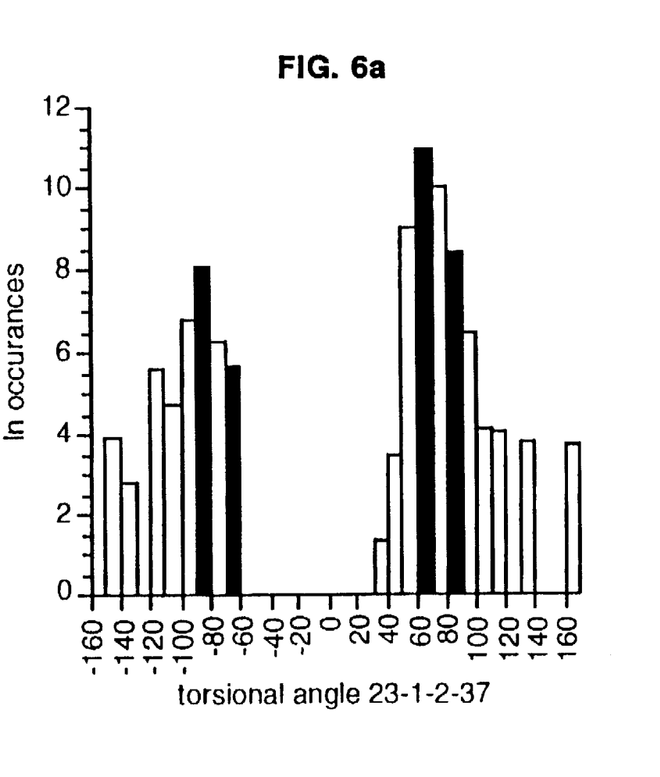
FIGS. 6a, 6b, 6c and 6d. Distribution of the 23-1-2-37 torsional angle after 1 and 10 million steps as obtained by MMC and JBW. Data were gathered every 10 steps and are presented as in occurrences vs. torsional value. Black bars indicate the location of energy minima on this scale (±65.2° and ±85.6° for the E=−92.1 KJ/mol and E=−88.5 KJ/mol pairs, respectively). 6a: MMC after $10^6$ steps; 6b: JBW after $10^6$ steps; 6c: MMC after $10^7$ steps; 6d: JBW after $10^7$ steps.
Figure 6B:
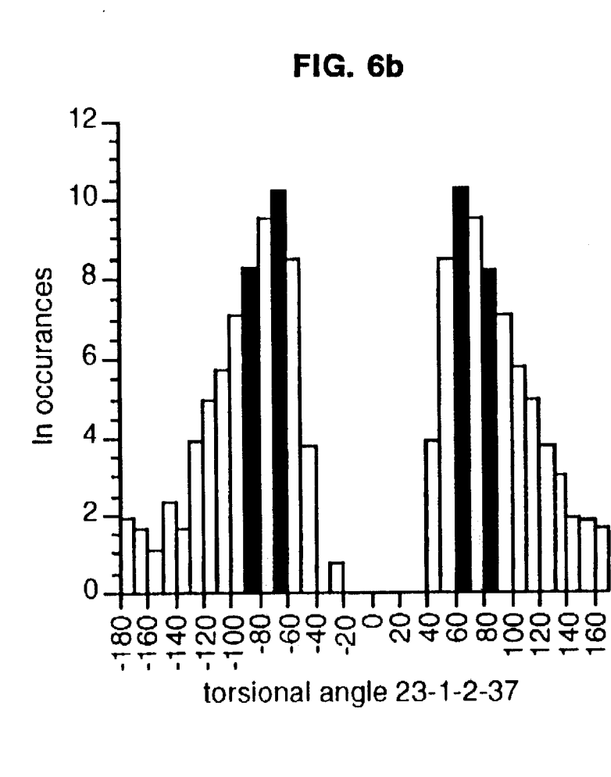
Figure 6C:
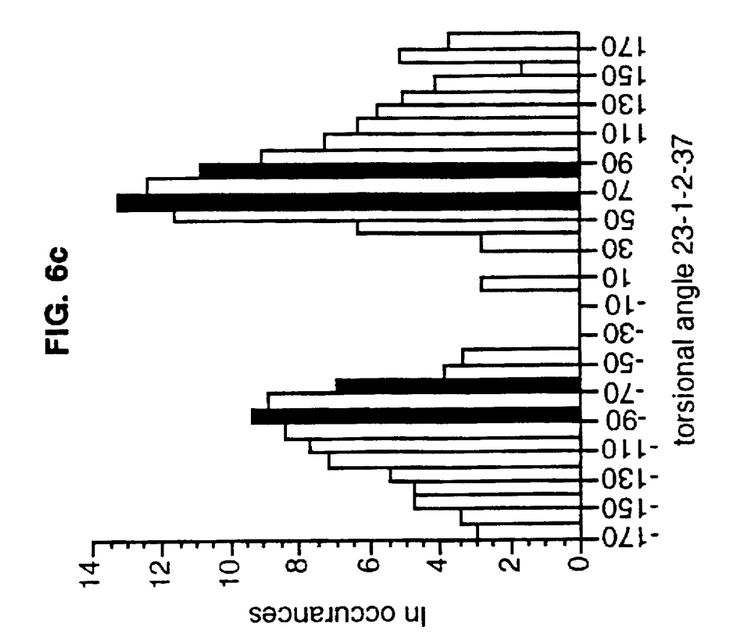
Figure 6D:
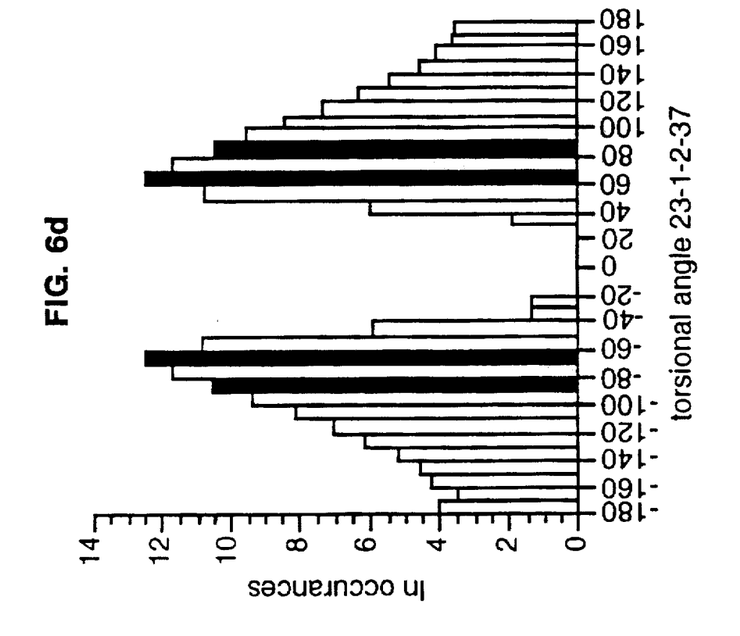

Potential as shown in FIG. 5b is a more demanding case, since the two identical paraboloidic wells occupy only 3.1 Å$^2$ (2.4%) of the potential surface total area below the E=100 KJ level (128.7 Å$^2$). Consequently, JBW is expected to converge much faster than MMC as indeed indicated by the data in Table 7. While it takes MMC, $1\times10^7$ steps to equalize the two populations to within 2 decimal places, JBW does it in only $7\times10^5$ steps, more than an order of magnitude faster.

TABLE 6

A comparison of wells population between MMC and JBW for potential 1a. Populations are monitored every $10^4$ steps and presented as the number of steps the simulation spends in each well divided by the total number of steps. Bold letters indicate the points were the two populations are equalized to within 2 decimal places.

| steps | Method | | | |
|---|---|---|---|---|
| | MMC | | JBW | |
| ($\times 10^4$) | well 1 | well 2 | well 1 | well 2 |
| 1 | 0.51 | 0.49 | 0.49 | 0.51 |
| 2 | 0.48 | 0.52 | 0.49 | 0.51 |
| 3 | 0.49 | 0.51 | 0.49 | 0.51 |
| 4 | 0.47 | 0.53 | 0.50 | 0.50 |
| 5 | 0.47 | 0.53 | 0.50 | 0.50 |
| 6 | 0.47 | 0.53 | 0.49 | 0.51 |
| 7 | 0.48 | 0.52 | 0.49 | 0.51 |
| 8 | 0.47 | 0.53 | 0.49 | 0.51 |
| 9 | 0.48 | 0.52 | 0.49 | 0.51 |
| 10 | 0.48 | 0.52 | 0.49 | 0.51 |
| 15 | 0.49 | 0.49 | 0.49 | 0.51 |
| 20 | 0.49 | 0.51 | 0.49 | 0.51 |
| 30 | 0.50 | 0.50 | 0.50 | 0.50 |
| 40 | 0.50 | 0.50 | 0.50 | 0.50 |
| 50 | 0.50 | 0.50 | 0.50 | 0.50 |
| 100 | 0.50 | 0.50 | 0.50 | 0.50 |
| 200 | 0.50 | 0.50 | 0.50 | 0.50 |
| 500 | 0.50 | 0.50 | 0.50 | 0.50 |

TABLE 7

A comparison of wells population between MMC and JBW for potential 1b. Populations are monitored every $10^4$ steps and presented as the number of steps the simulation spends in each well divided by the total number of steps. Bold letters indicate the points were the two populations are equalized to within 2 decimal places.

| steps | Method | | | |
|---|---|---|---|---|
| | MMC | | JBW | |
| ($\times 10^4$) | well 1 | well 2 | well 1 | well 2 |
| 1 | 0.65 | 0.35 | 0.51 | 0.49 |
| 5 | 0.43 | 0.57 | 0.49 | 0.51 |
| 10 | 0.53 | 0.47 | 0.50 | 0.50 |
| 20 | 0.47 | 0.53 | 0.49 | 0.51 |
| 30 | 0.45 | 0.55 | 0.50 | 0.50 |
| 40 | 0.46 | 0.54 | 0.50 | 0.50 |
| 50 | 0.45 | 0.55 | 0.49 | 0.51 |
| 70 | 0.49 | 0.51 | 0.50 | 0.50 |
| 100 | 0.50 | 0.50 | 0.50 | 0.50 |
| 150 | 0.50 | 0.50 | 0.50 | 0.50 |
| 200 | 0.50 | 0.50 | 0.50 | 0.50 |
| 300 | 0.50 | 0.50 | 0.50 | 0.50 |
| 500 | 0.51 | 0.49 | 0.50 | 0.50 |
| 1000 | 0.50 | 0.50 | 0.50 | 0.50 |
| 10000 | 0.50 | 0.50 | 0.50 | 0.50 |
| 12000 | 0.50 | 0.50 | 0.50 | 0.50 |

When the potential surface is non-symmetric (potential 3c), the more traditional average energy and standard deviation can be used to assess the convergence rate. Once more, due to the fact that most of the surface was not populated, JBW was predicted to be much more efficient than MMC, as indeed can be inferred from the data in Table 8. Convergence to within 0.5% from the "correct" results (3.68–3.72 and 3.76–3.80 for the average energy and standard deviation, respectively) was achieved by MMC after $4\times10^7$ steps and by JBW, after $1\times10^6$ steps, 40 times faster.

TABLE 8

A comparison of average energy (PE; KJ/mol) and standard deviation (SD) between MMC and JBW for potential 1c. Data are monitored every $10^5$ steps. Bold letters indicate the points were both PE and SD are converged to within 0.5% of the correct result (see text).

| steps | Method | | | |
|---|---|---|---|---|
| | MMC | | JBW | |
| ($\times 10^5$) | PE | SD | PE | PE |
| 1 | 4.45 | 3.57 | 3.77 | 3.79 |
| 5 | 4.06 | 3.93 | 3.67 | 3.74 |
| 10 | 3.91 | 3.91 | 3.72 | 3.77 |
| 20 | 3.75 | 3.83 | 3.70 | 3.76 |
| 50 | 3.78 | 3.78 | 3.69 | 3.76 |
| 100 | 3.67 | 3.80 | 3.69 | 3.77 |
| 200 | 3.69 | 3.78 | 3.70 | 3.77 |
| 300 | 3.74 | 3.81 | 3.69 | 3.76 |
| 400 | 3.70 | 3.80 | 3.70 | 3.77 |
| 500 | 3.69 | 3.79 | 3.70 | 3.77 |
| 700 | 3.71 | 3.79 | 3.70 | 3.77 |
| 1000 | 3.69 | 3.78 | 3.70 | 3.78 |
| 1200 | 3.70 | 3.78 | 3.70 | 3.78 |

Tests with molecular systems

To test the new JBW method on a more chemically relevant system, it was incorporated into the MacroModel V4.5 distribution of BatchMin. The method was first modified to treat the torsional space and later, generalized to the molecular space to enable the simulation of complexes and host-guest compounds. Two simple systems, pentane and a glycine zwitterion—methanol complex were chosen to study the ability of both methods to generate the correct (canonical) ensemble. Following a conformational search, long ($90\times10^6$ steps) MMC and JBW simulations were run on the two systems using the united atom AMBER force field. For pentane, the two torsional degrees of freedom where randomly changed by the MC procedures, while for the glycine zwitterion—methanol complex, only the relative positions of the two molecules were altered leaving the internal degrees of freedom intact (i.e., rigid). In order to judge the ensembles generated, the first four moments of the potential energy distribution (average, standard deviation, skew and kurtosis) were accumulated. The results, summarized in Table 9, confirm that the two different simulations generated essentially the same canonical ensemble, the acceptance rates obtained with JBW, being once more higher.

TABLE 9

A comparison of average energy (PE; KJ/mol), standard deviation (SD), skew (SK), kurtosis (KU) and acceptance rate (% acceptance) between MMC and JBW for pentane and the glycine zwitterion - methanol complex.

| System | pentane | | glycine zwitterion - methanol | |
|---|---|---|---|---|
| Method | MMC | JBW | MMC | JBW |
| PE | 3.82 | 3.81 | −172.47 | −172.51 |
| SD | 3.40 | 3.38 | 5.47 | 5.43 |
| SK | 1.30 | 1.28 | 0.49 | 0.51 |
| KU | 2.75 | 2.70 | 1.46 | 1.44 |
| % acceptance | 0.070 | 0.410 | 0.005 | 0.064 |

As a more chemically demanding system, in which JBW is expected to have a distinct advantage over MMC, the podand ionophore complex shown in FIGS. 5a and 5b was studied. A rigid body (i.e., constraining all internal degrees of freedom) conformational search, performed with the united atom AMBER force field resulted in two chemically different structures having energies of −92.1 KJ/mol and −88.5 KJ/mol. Due to the C2 symmetry of the host, each guest can occupy one of two topologically distinct binding sites, leading to a total of 4 conformers. Starting from the global minimum (E=−92.1 KJ/mol), long ($10^7$ steps) MMC and JBW simulations were subsequently run to determine the relative efficient with which both methods sample the conformational space. As with the symmetric 1D and 2D potential surfaces, the average potential energy can't be taken as a measure of convergence. Thus, once more wells population was resort to, determined by sampling 2000 structures along the trajectory followed by energy minimization. In addition, the distribution of a single improper torsional angle (23-1-2-37, see FIGS. 6a, 6b, 6c and 6d) whose values are ±65.2° and ±85.6° for the E=−92.1 KJ/mol and E=−88.5 KJ/mol pairs, respectively, was monitored. The relevant data are shown in Table 10 and FIGS. 6a, 6b, 6c and 6d and lead to the following conclusions:

1. Based on the energetic values it is to be concluded, once more, that both methods generate the same (canonical) ensemble (the small differences, particularly in the forth moment, are attributed to incomplete convergence).

2. In 10 million steps, MMC sampled only half of the potential surface as is evident from the zero population of wells 2 and 4. In contrast, JBW uniformly scanned the entire surface as suggested by the similar populations of identical wells (well 1=920, well 2=960; well 3=55, well 4=66).

Accordingly, the final average values of the 23-1-2-37 torsion, which by symmetry should be 0°, area 63.6° and −1.6° for MMC and JBW, respectively.

3. For this particular system, JBW converges at least an order of magnitude faster than MMC. This is evident from the data in FIGS. 6a, 6b, 6c and 6d where the distribution of the 23-1-2-37 torsional angle after 1 and 10 million steps as obtained by both methods are compared. While JBW displays the expected symmetry around 0° after 1 million steps, MMC fails to do so even after 10 million steps (note the logarithmic scale in FIGS. 6a, 6b, 6c and 6d).

TABLE 10

A comparison of average energy (PE; KJ/mol), standard deviation (SD), skew (SK), kurtosis (KU), well populations (well 1–4), average 23-1-2-37 torsional angle (<23-1-2-37>) and acceptance rate (% acceptance) between MMC and JBW for the host - guest complex. Well populations were calculated by sampling 2000 structures along the trajectory at regular intervals, and assigning them into the different wells by energy minimization.

| Method | MMC | JBW |
|---|---|---|
| PE | −84.23 | −84.10 |
| SD | 4.57 | 4.74 |
| BK | 1.15 | 1.10 |
| KU | 2.10 | 1.72 |
| well 1 | 1944 | 920 |
| well 2 | | 960 |
| well 3 | 57 | 55 |
| well 4 | | 66 |
| <23-1-2-37> | 6.36 | −1.6 |
| % acceptance | 0.001 | 0.066 |

In conclusion hardware suitable for carrying out the MC/SD and/or JBW simulation methods could include any fast digital processor. In particular, UNIX workstations (Silicon Graphics IRIS, INDIGO, INDIGO$^2$; IBM RS/6000; Hewlett Packard Model 9000) and supercomputers (e.g. CRAY Y-MP; IBM SM1 and SM2) would be particularly suitable. For graphical display of results, IBM RS/6000 and Silicon Graphics IRIS, INDIGO or INDIGO$^2$ graphics workstations can be used.

What is claimed is:

1. A method of using a computer processor for generating possible representations of a molecule to design a molecular receptor comprising the steps of:

a) selecting a first representation of a conformation of the molecule characterized by a first set of coordinates associated with each atom representation in the molecule by the presence of a pattern of forces among such atom representations and by a series of intrinsic forces associated with each atom representation;

b) varying the pattern of forces among such atom representations in a non-random manner and randomly varying the series of intrinsic forces associated with each atom representation so as to generate a second representation of a conformation of the molecule characterized by a second set of coordinates associated with each atom representation in the molecule, by a second pattern of forces among each atom representation and by a second series of intrinsic forces associated with each atom representation; and c) randomly varying the second set of coordinates so as to obtain a third set of coordinates thereby generating the molecular receptor.

2. A method for using a computer processor for generating a series of possible representations of a molecule to design a molecular receptor which comprises generating a possible representation of a conformation using the method of claim 1, and then repeating such method to obtain one or more additional possible representations of conformations, the selected first representation of a conformation of step (a) of each such repeated method being a possible representation of a conformation previously generated.

* * * * *